United States Patent [19]

Peterson

[11] Patent Number: 4,533,761

[45] Date of Patent: Aug. 6, 1985

[54] METHOD FOR PREPARING BUTENE DIETHERS

[75] Inventor: Marvin L. Peterson, Woodstown, N.J.

[73] Assignee: E. I. Du Pont de Nemours and Company, Wilmington, Del.

[21] Appl. No.: 620,317

[22] Filed: Jun. 13, 1984

Related U.S. Application Data

[63] Continuation-in-part of Ser. No. 519,212, Aug. 2, 1983, abandoned, which is a continuation of Ser. No. 359,044, Mar. 17, 1982, abandoned.

[51] Int. Cl.$^3$ ............................................. C07C 41/06

[52] U.S. Cl. .................................................. 568/673
[58] Field of Search ......................................... 568/673

[56] References Cited

FOREIGN PATENT DOCUMENTS 1138366  1/1969  United Kingdom ................. 568/673

Primary Examiner—J. E. Evans

[57] ABSTRACT

Butene diethers are prepared by the reaction of butadiene and an alkanol, in a medium containing iodide ions and copper ions having an average oxidation state of 1–2.

2 Claims, No Drawings

METHOD FOR PREPARING BUTENE DIETHERS

CROSS-REFERENCE TO RELATED APPLICATIONS

This application is a continuation-in-part of application Ser. No. 519,212, filed Aug. 2, 1983, as a continuation of application Ser. No. 359,044, filed Mar. 17, 1982, both now abandoned.

DESCRIPTION

Technical Field

This invention relates to a method for preparing butene diethers. It is more particularly directed to a method for preparing butene diethers represented by the structure.

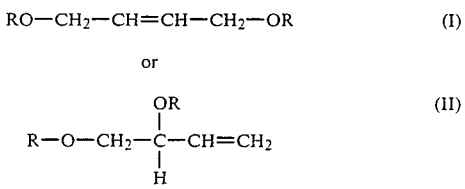

where R is a linear or branched alkyl radical of 1-4 carbon atoms.

BACKGROUND OF THE INVENTION

Furan is a commodity in the chemical industry, widely used as a starting material for the preparation of tetrahydrofuran. It has in the past been made from pentoses which occur naturally in corn or in oat hulls. More recently, a method was disclosed in U.S. Pat. No. 4,257,960 whereby furan can be prepared from butene diethers.

British Pat. No. 1,138,366 discloses a method for preparing such diethers, using as a catalyst a salt or co-ordination compound of palladium, platinum, nickel, iron or cobalt (all metals of Group 8 of the periodic Table) together with a copper redox system.

The present invention provides a method for preparing the butene diethers without using Group 8 metal catalysts, i.e., in a medium substantially free of these metals.

DETAILED DESCRIPTION OF THE INVENTION

The diethers of structures (I) and (II) can be prepared according to the invention by the reaction of 1,3-butadiene and an alkanol, with the alkanol also acting as the reaction medium.

The 1,3-butadiene used can be of any grade available in the marketplace.

The alkanol can be any one containing 1-4 carbon atoms. As with the butadiene, the alkanol can be of any grade available in the marketplace.

The reaction medium must contain iodide ions and copper ions.

The iodide ions may be provided by any iodine compound soluble enough in the medium to provide an effective concentration of iodide ions, ordinarily $1 \times 10^{-12} - 0.5$ mole per liter of medium, and preferably 0.001-0.2 mole per liter. Illustrative of such compounds are the alkali metal iodides, cuprous iodide, ferrous iodide, and organic iodides such as methyl iodide and ethyl iodide. Of these, the alkali metal iodides, especially sodium iodide and potassium iodide, are preferred. Mixtures of iodides can also be used.

The copper ions should have an average oxidation stage of 1-2, that is to say, they should be present as $Cu^{+2}$ ions and as $Cu^{+1}$ ions, which are provided by combinations of cupric and cuprous salts. The $Cu^{+2}/Cu^{+1}$ mole ratio in the system will normally be $100/1-\frac{1}{2}$, preferably 25/1-1/1.

These copper ions may be provided by any copper compounds or mixtures of copper compounds soluble enough in the reaction medium to provide an effective concentration of copper ions, ordinarily 0.1-10 moles per liter of reaction medium (total copper ion content) and preferably 0.5-3 moles per liter (total copper content). Illustrative of such copper compounds are the halides, especially cupric chloride, cupric bromide, cuprous chloride, cuprous bromide and cuprous iodide. Copper salts of organic acids, such as the acetates, propionates, pivalates, formates, succinates, adipates, trifluoroacetates and sulfonates may also be used. Copper halides are preferred.

It may be desirable to have a solubilizing agent in the medium to help keep the requisite number of $Cu^{+1}$ ions dissolved in it. This agent can be any organic or inorganic compound which forms a complex with $Cu^{+1}$ ions soluble enough in the medium to form a 0.2-3 molar solution. Illustrative of such agents are the alkali metal halides, the alkaline earth metal halides, the ammonium halides, and the iron halides. Solubilizing agents preferred for use are the alkali metal halides, especially calcium chloride. Mixtures of solubilizing agents can also be used.

The solubilizing agent is ordinarily present in the medium at a concentration of about 0.01-5 moles per liter, preferably 0.3-5 moles per liter.

The process of the invention may be begun by dissolving the iodine compound, the copper compounds and the solubilizing agent (if one is used) in the alkanol of choice. This solution is then brought to and held at an elevated temperature, ordinarily 25°-75° C. and preferably 25°-50° C., and at a pressure of atmospheric-350 kPa, preferably with stirring, while butadiene gas (or liquid) is fed into it. The rate of butadiene feed is ordinarily a matter of choice, and will, in the usual case, be 50-500 ml of gas per liter of reaction medium per hour. Butadiene feed is continued until the reaction, in essence, is complete, as manifested by the solution no longer absorbing butadiene.

As the reaction proceeds, the $Cu^{+2}$ ions are reduced to $Cu^{+1}$ ions, and the reaction slows unless the $Cu^{+2}$ ions are regenerated or replenished. It may therefore be desirable to do this by passing oxygen through the medium. The oxygen can be introduced as molecular oxygen or, to minimize the risk of explosion, as a mixture of oxygen with an inert gas. Any gas which is inert to the reaction can be used. Nitrogen, helium and carbon dioxide are illustrative. The use of air is also satisfactory.

The regeneration can be done in situ or can be carried out in a separate reactor, and can be accomplished while the reaction proceeds if this seems appropriate. Oxygenation is continued until oxidation of the $Cu^{+1}$ ions to $Cu^{+2}$ ions has brought the $Cu^{+2}/Cu^{+1}$ mole ratio to its original level, as determined potentiometrically. Alternatively, the proper $Cu^{+2}/Cu^{+1}$ mole ratio can be maintained in the reaction medium by continuous oxygenation.

The product of the process of the invention is normally a mixture of the butene diethers of structures (I) and (II). This mixture can be separated from the reaction medium by making the medium basic, thus precipitating copper, and then separating the butene diether mixture from the medium by distillation. Alternatively, the mixture can be separated from the medium by extraction with a suitable solvent such as methylene chloride. The butene diethers can then be separated from one another by conventional techniques such as fractional distillation.

In the following, all parts are by weight unless otherwise indicated.

EXAMPLE 1

Best Mode

Into 500 parts by volume of isopropanol were dissolved

| | |
|---|---|
| $CuCl_2 \cdot 2H_2O$ | 170 parts |
| CuCl | 40 parts |
| $CaCl_2$ | 66 parts |
| HCl (37% in water) | 20 parts by volume |
| KI | 4 parts |

The resulting solution was brought to and held at about 50° C., with stirring, while butadiene gas was fed into it until the solution had an oxidation potential of 292 mv (vs. a saturated calomel electrode) as measured by a platinum wire electrode.

The butadiene feed was then discontinued and air fed into the solution until it had a potential of 526 mv. The butadiene feed was then resumed until the potential of the solution was 321 mv.

The feed was then stopped and solids were filtered from the solution, whose pH was brought to 3.5 with 50% aqueous NaOH. Solids were again filtered off, and the two layers which formed in the filtrate were combined.

Individual products in the resulting solution were separated by fractional distillation and identified by gas chromatography, mass spectrometry and nuclear magnetic resonance spectrometry as 3,4-diisopropyloxy-1-butene and 1,4-diisopropyloxy-2-butene.

EXAMPLE 2

Into 500 parts by volume of methanol were dissolved

| | |
|---|---|
| $CuCl_2 \cdot 2H_2O$ | 85 parts |
| CuCl | 20 parts |
| $CaCl_2$ | 66 parts |
| HCl (37% in water) | 4 parts by volume |
| KI | 4 parts |

The resulting solution was brought to and held at 40° C., with stirring, while a mixture of 80 parts of volume of butadiene gas in 400 parts by volume of air was fed into it over a six-hour period. During this period, the solution was maintained at a potential of 420 mv (vs. a standard calomel electrode).

The air flow was then stopped and butadiene alone was fed into the solution until the potential was brought to 280 mv. The solution was then filtered, brought to pH 5.7 with aqueous 50% NaOH and then distilled to removal methanol. The remaining liquid formed two layers—an aqueous layer and an organic product layer which contained 44% of 3,4-dimethoxy-1-butene and 37% by weight of 1,4-dimethoxy-2-butene (as identified by their infrared and nuclear magnetic resonance spectra), which were separated from each other by fractional distillation.

INDUSTRIAL APPLICABILITY

The butene diethers produced according to the process of the invention can be used as starting materials for the preparation of furan by the method shown in U.S. Pat. No. 4,257,960.

I claim:

1. In a process for preparing a butene diether represented by the structure

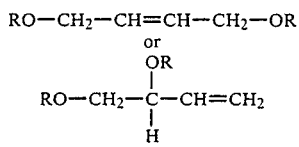

where R is a linear or branched alkyl radical of 1-4 carbon atoms, from 1,3-butadiene and a linear or branched alkanol of 1-4 carbon atoms, the use of a catalyst system consisting of an alkali metal iodide and copper compounds, which are copper halides or copper salts of organic acids and which will provide copper ions having an average oxidation state of 1-2.

2. The process of claim 1 wherein the alkali metal iodide is potassium iodide.

* * * * *